United States Patent [19]

Peterson

[11] 4,246,568
[45] Jan. 20, 1981

[54] APPARATUS AND METHOD OF PERSONAL IDENTIFICATION BY FINGERPRINT COMPARISON

[76] Inventor: Vernon L. Peterson, 820 Hill St., Belmont, Calif. 94002

[21] Appl. No.: 967,621

[22] Filed: Dec. 8, 1978

[51] Int. Cl.³ ............................................. G06K 9/20
[52] U.S. Cl. ........................ 340/146.3 E; 340/146.3 Q
[58] Field of Search .................. 340/146.3 E, 146.3 Q; 356/71

[56] References Cited

U.S. PATENT DOCUMENTS

| | | | |
|---|---|---|---|
| 3,200,701 | 8/1965 | White | 340/146.3 E |
| 3,292,149 | 12/1966 | Bourne | 340/146.3 E |
| 3,516,059 | 6/1970 | Hindman et al. | 340/146.3 E |
| 3,576,534 | 4/1971 | Steinberger | 340/146.3 Q |
| 3,582,898 | 6/1971 | Lemay | 340/146.3 Q |
| 3,584,958 | 6/1971 | Miller et al. | 340/146.3 E |
| 3,975,711 | 8/1976 | McMahon | 340/146.3 E |
| 4,015,240 | 3/1977 | Swonger et al. | 340/146.3 E |

*Primary Examiner*—Leo H. Boudreau
*Attorney, Agent, or Firm*—Leonard R. Cool

[57] ABSTRACT

Finger prints of authorized personnel are initially stored in digital form in a memory. Subsequently, personal identification is obtained by matching the fingerprints of individuals with the stored prints. The individual places his finger in an activator which indexes the finger and turns on the equipment. The fingerprint image may be refleted directly into an electronic image sensor or it may be initially impressed upon a tape for later image scanning. In either case, the electronic image sensor scans the fingerprint image and converts the optical characteristic of the print into a plurality of picture elements, and provides an electrical signal representative of each of the picture elements at its output. The picture elements are converted either in the electronic image sensor or in an analog to digital converter into a digital code representative of each picture element. These digital codes are entered into a temporary storage for comparison with the fingerprints contained in the memory. Handshaking circuits cause the image fingerprint to be compared with each stored fingerprint until either a match is obtained or the image has been compared with each print contained in the memory and no match was made. The match or no-match condition causes, respectively, a go or no-go output indication which may be used to perform any number of desired functions.

5 Claims, 7 Drawing Figures

APPARATUS AND METHOD OF PERSONAL IDENTIFICATION BY FINGERPRINT COMPARISON

BACKGROUND OF THE INVENTION

1. Field of the Invention

This invention relates to pattern recognition apparatus and, more particularly, to such apparatus which is utilized in situ for automatically comparing stored fingerprints with a new fingerprint image.

2. Description of the Prior Art

Previously known systems for automatically identifying fingerprint images have as their objective the location of certain points in the image that are uniquely characteristic of an individual's fingerprint. These points are termed minutiae and consist of line or ridge endings or bifurcations existing in the total contour pattern of the fingerprint. One such system is disclosed in U.S. Pat. No. 4,015,240, inventors C. W. Swonger et al., entitled "Pattern Recognition Apparatus". In actual field use, such systems must accurately identify these characteristic points despite the wide variations introduced in the process of obtaining the fingerprint impression or image. As is well known, the inked fingerprint impression is characterized by wide variations in the inking of the finger, variations in pressure during the rolling of the print and twisting or other smearing actions which tend to degrade the quality of the fingerprint impression.

SUMMARY OF THE INVENTION

It is therefore a principal object of the invention to overcome the problem of reproducibility of the fingerprint image so as to facilitate comparison for personal identification.

A system for classifying personnel by means of fingerprints to determine whether or not they are authorized includes the storing of fingerprint characteristics of authorized personnel, alignment of the finger of the person to be classified so as to consistently present the appropriate view of the image fingerprint for comparison, opto-electronic elements for reading the fingerprint characteristics of the person to be classified, and a technique for comparing the image fingerprint with each of the stored fingerprints, if necessary, so as to determine if the image fingerprint is authorized.

DETAILED DESCRIPTION OF THE INVENTION

An understanding of the operation of a preferred embodiment of the invention may be obtained from the following detailed description taken in conjunction with the accompanying drawings.

Figure 1:
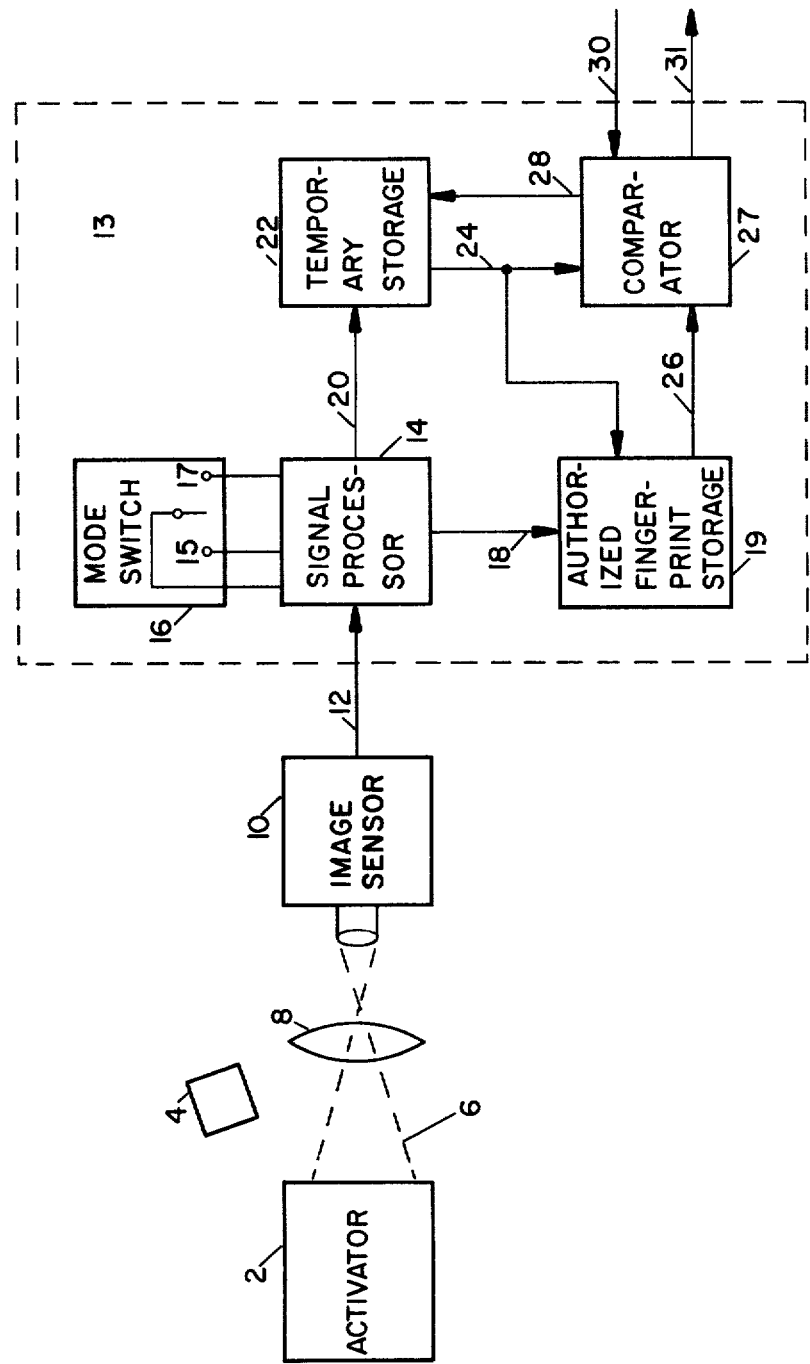
FIG. 1 is a block diagram of a preferred embodiment of the invention showing the basic elements which make up the classification system.

Referring now to FIG. 1, it is to be understood that activator 2 performs several functions as will be explained in more detail below. First, activator 2 accepts one or more fingers of the person to be classified and by means of guides and force requirements aligns the finger(s) so that the fingerprints to be analyzed are illuminated by light source 4 and the reflected fingerprint image is seen by image sensor 10 via optical path 6. The optical path is symbolic, including lens 8, and it is to be understood that any optical technique may be used which would make the fingerprint image clearly visible to image sensor 10. Further, a shutter or blocking device, not shown, may be inserted between the activator 2 and optical path 6 to prevent insertion of foreign materials etcetera when not in use. As mentioned above, activator 2 requires that the person to be classified insert his finger in a guide and then exert certain pressures. These actions not only cause the finger to be properly aligned in each application, but also close power energizing contacts to complete the power circuit. While more than one fingerprint image may be used in the evaluation, only one fingerprint is actually necessary, and in the following discussion only one fingerprint image is considered, thus simplifying the discussion.

Image sensor 10, which may be a regular vidicon tube but is preferably a device such as the General Electric type TN2200 Automation Camera, converts picture elements (pixels) of the optical image into electrical signals. Such optical-to-electrical conversion is well-known and will not be considered in detail here. However, it is important to note that the proper operation of the invention requires that (a) the optical system be designed to be compatible with the image sensor in order to obtain the optimum transfer of information, and, (b) the number of pixels must be adequate to provide good definition of the image fingerprint. The GE TN2200, which contains an array of $128 \times 128 (16,384)$ pixels has been found to provide adequate definition.

The electrical signals from image sensor 10 pass along path 12 to signal processor 14. To facilitate storage and comparison, each pixel is converted from analog to digital in form. Where the TN2200 is used, the conversion may be accomplished in the Automation Camera. Otherwise, the analog signal obtained from the optical-to-electrical process may be amplified and then converted into a digital representation of the analog signal level for each pixel element in the signal processor 14.

The digital signals from processor 14 will either pass to authorized print storage 19, when mode switch is in the first position, in which case the digital representation of each fingerprint is stored for future comparison;

or will pass via path 20 to temporary storage 22. In either case the storage may be accomplished by well known techniques, including the use of computer programs and/or microprocessors. Further it is to be understood that signal processor 14 in conjunction with mode switch 16 and authorized fingerprint storage 19 will search for an authorized print which is to be eliminated from authorized storage 19, and will operate to either eliminate this print or to replace same with another authorized fingerprint.

Once the authorized fingerprints have been stored mode switch 16 is shifted to the second position, and the armature is now touching contact 17. Now when a person places a finger in activator 2, the digital representation of the image fingerprint passes through signal processor along path 20 to temporary storage 22. Temporary storage 22 may consist of a number of registers or other memory storage devices which will accept a serial binary input. When the digital representation has been stored the registers are scanned and the pixel data is supplied to one input terminal of comparator 27 along path 24. The most significant bit of the first pixel element provides a hand shaking input via path 24 to authorized fingerprint storage 19. The digital representations of the authorized fingerprints are fed to comparator via path 26. Following a comparison with each print, a reset pulse is applied to temporary storage 22 via path 28 so as to reset the image fingerprint for comparison with the next authorized fingerprint. However, if either a correct comparison is made or if the complete file of authorized fingerprints have been compared without obtaining a correct comparison, the data passed along path 28 set the register so that the image fingerprint will be erased and not further compared. Also, a correct comparison will cause a GO signal to appear on path 30, whereas an incorrect comparison with all of the fingerprints in the file will cause a NO-GO signal to appear on path 31. The GO and NO-GO signals may be used to perform any number of functions. For example, the GO signal can be used to open an access door for authorized persons and record the time of entry, et cetera. The NO-GO signal may sound an alarm or perform other desired functions.

Figure 2:
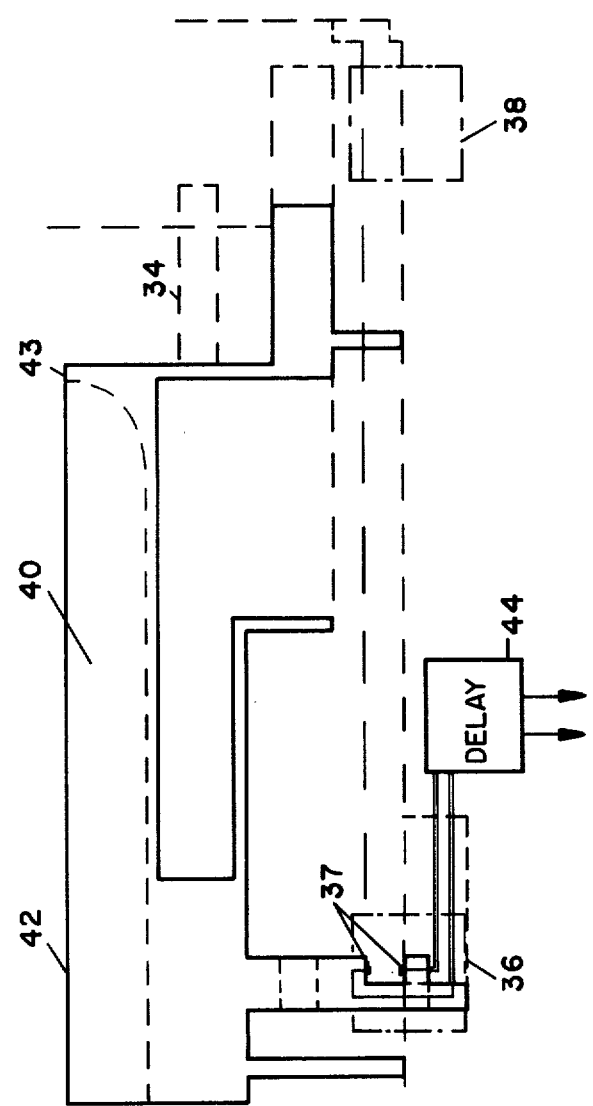
FIG. 2 is a schematic diagram showing the activator in simplified form in order to illustrate the power switching, delay and pressure functions performed by the activator.

FIG. 2 is a simplified diagram showing the switch and pressure forces employed with activator 2 for energizing the system and for aligning the finger of the person to be classified. As will be shown in more detail later finger guide 42 accepts the finger in the recessed portion shown by the dotted lines. The end of the finger is pressed against the raised portion 43 of finger guide 42, and is pushed against the pressure device 34 for a distance of about 3/16th of an inch. This causes the person to put adequate forward pressure for alignment purposes, and when so moved finger guide 42 moves clear of fixed support 32 and rests on pressure devices 36 and 38. Once clear of support 32, downward pressure will move the finger guide 42 down against the pressure devices 36 and 38, and, again, a movement downward of about 3/16th of an inch will close contacts 37 to complete the power circuit, thereby energizing the system. Delay means 44 latches up when the electrical circuit is initially closed. After a delay interval, selected so as to permit a complete comparison to be performed, the latch is released and the circuit is now ready to accept a new print. In both cases the pressure required is just sufficient so that the finger is forced to be in the correct position for displaying the fingerprint of the person to be classified.

Figure 3:
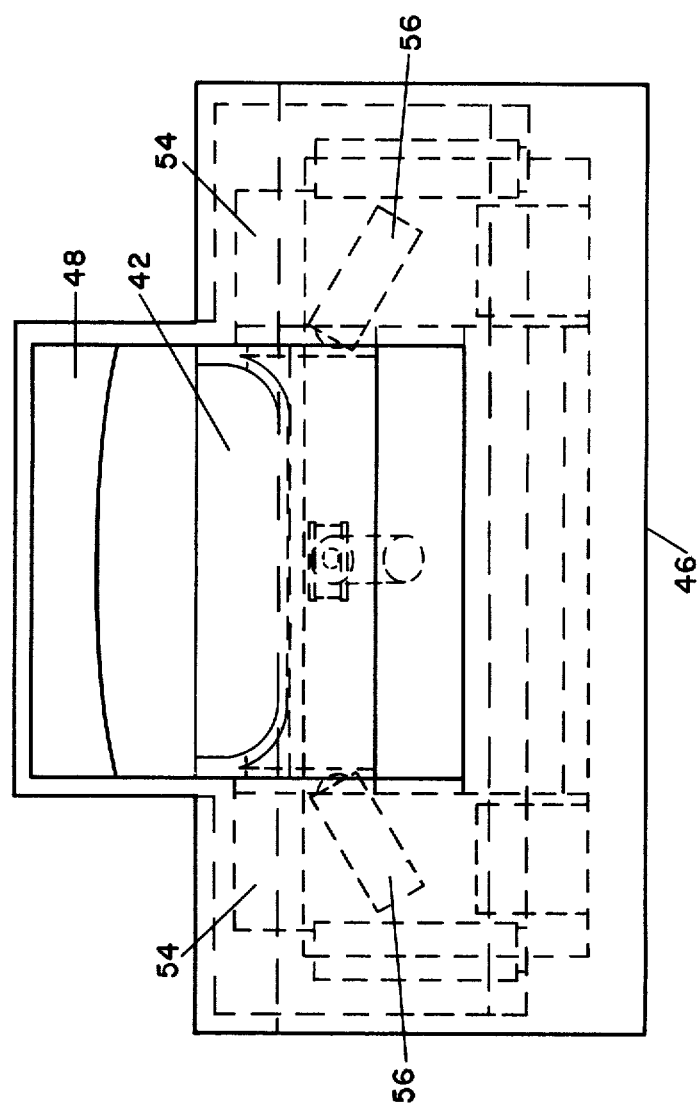
FIG. 3 is an end view of the activator, not to scale, showing base member 46 which support finger guide 48 having fingernail recess 50. A portion of one lighting technique, which illuminates the finger when it is positioned in finger guide 48, is shown in dotted form and is more clearly illustrated in FIG. 5.
Figure 4:
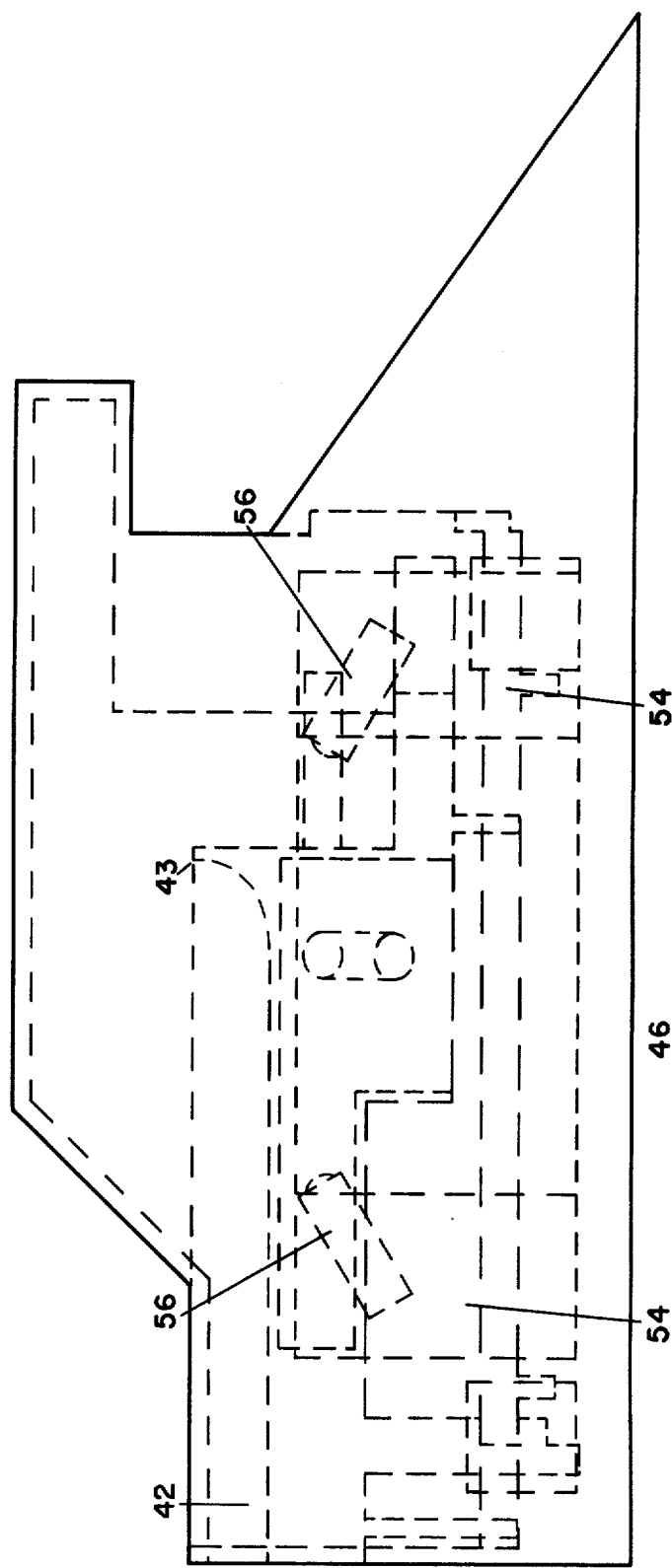
FIG. 4 is a side view of the activator illustrating in more detail the position and interrelation between the finger guide 48 and base member 46. Also shown is the curved end 52 which is in contact with the end of the finger when the finger is properly inserted in the guide.
Figure 5:
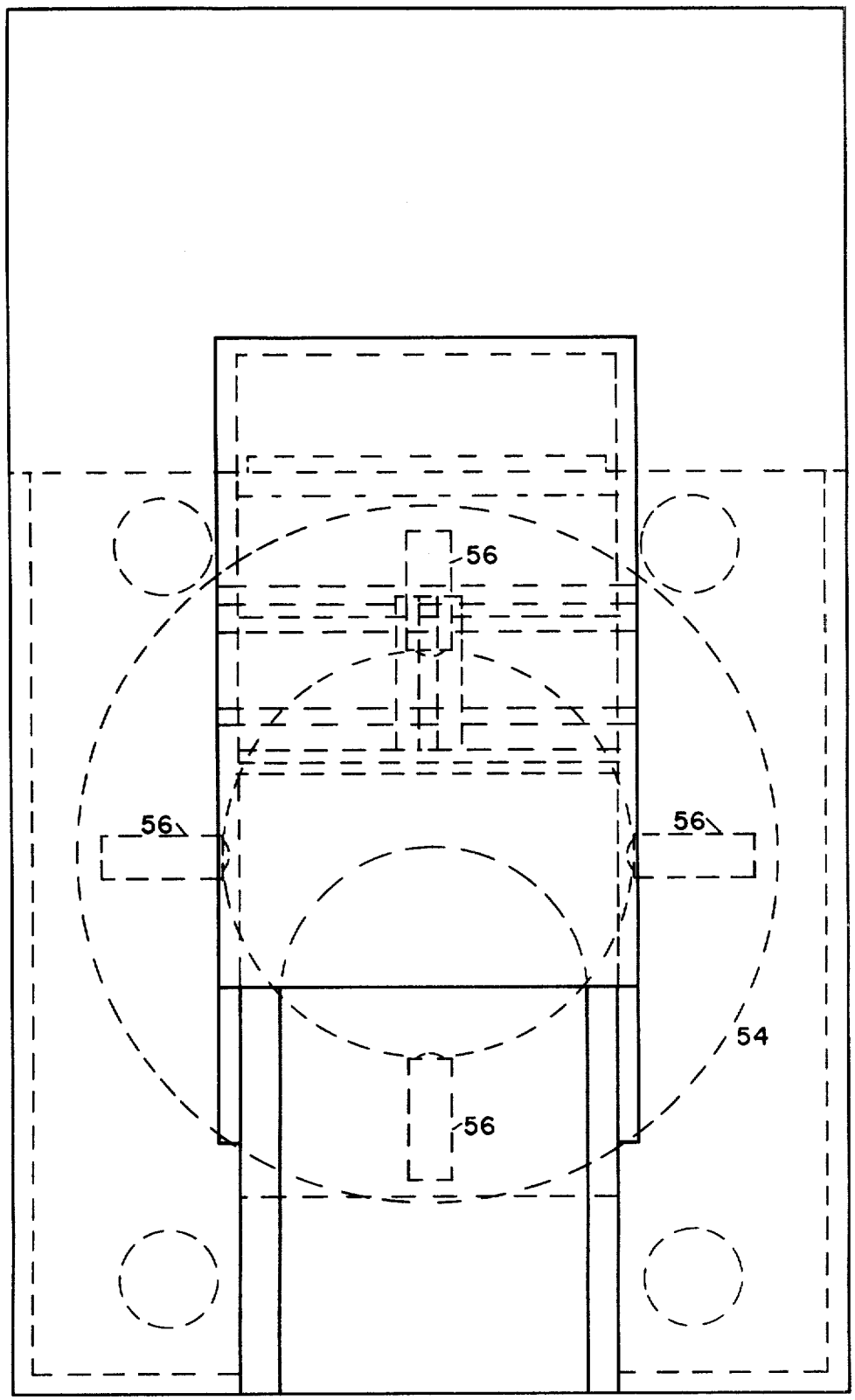
FIG. 5 is a top view of the activator and illustrates the circular optical tube 54 and light sources 56.
Figure 6:
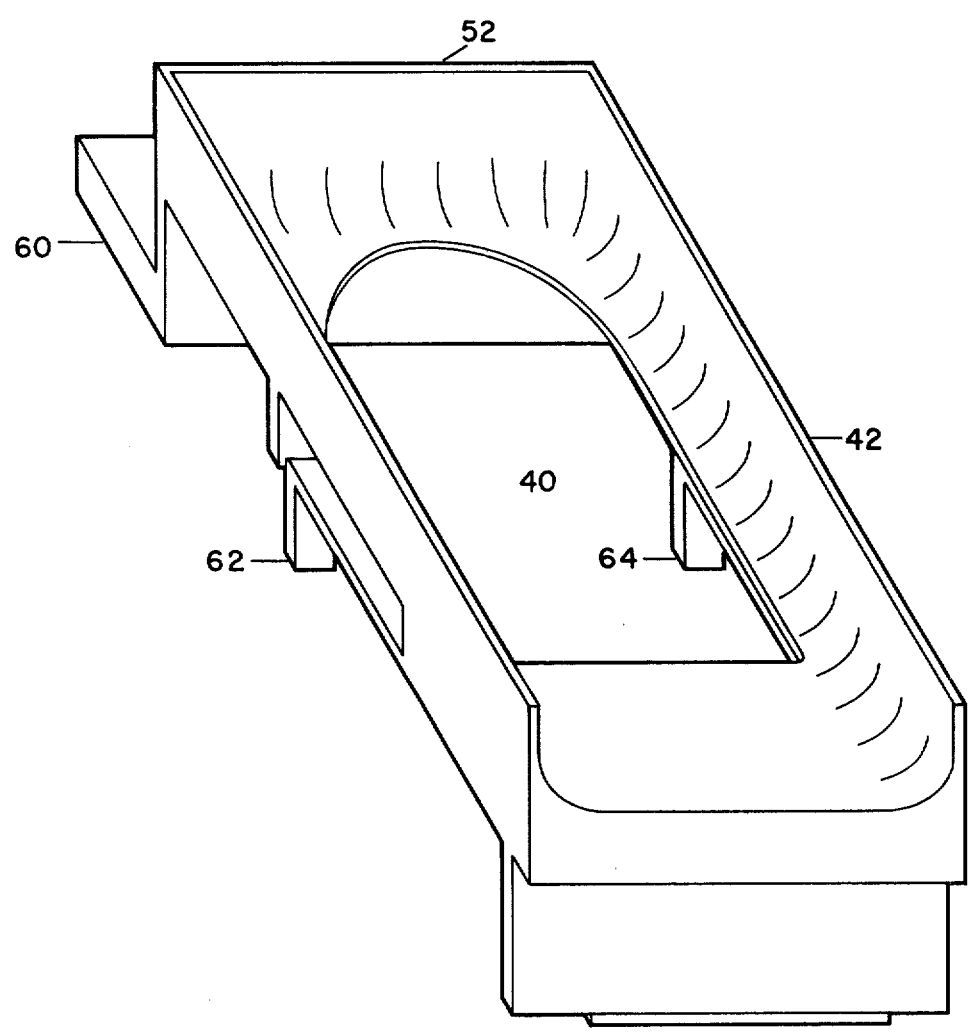
FIG. 6 is a perspective view of the finger guide 48 and illustrates the curved sides which support and align the finger, the curved end 52, apertures 58, end slide 60 and side slides 62 and 64.

FIG. 3 is an end view of actuator 2 showing in more detail the relationship of the base 46, finger guide 42, and optical tube 54 which provides mounting for light sources 56. Finger guide 42 is slideably engaged in a groove in base 46 so that it can move forward and then down as previously described. The finger guide 42 includes a recess 48 which is designed to accept the finger nail of the person. A side view of the actuator 2 is shown in FIG. 4 to more clearly illustrate the manner in which finger guide 42 is slideably engaged with base 46. The pressure devices and switch contacts are not show in order to simplify the drawing. A top view of the actuator 2 is shown in FIG. 5 to more clearly illustrate the location of optical tube 54 and light sources 56. It is clear from the figure that the light sources are symmetrically disposed about the optical tube 54 and they are angled as shown in FIGS. 3 and 4 so as to direct the light rays on the finger portion exposed through aperture 40 of finger guide 42. FIG. 6 is a perspective view of the finger guide 42 illustrating the shape of aperture 40 i.e., the desired curvature of the sides of the guide for correctly seating the finger and the curvature of end portion 52 which acts as a finger stop. Aperture 40 is about ⅜ths of an inch wide, and about 1 (one) inch long with the part adjacent the end portion 52 being curved, as shown, to engage and support the end of the finger, thus maintaining proper alignment. Surfaces 60, 62 and 64 provide the sliding surface for finger guide 42. It is apparent from the foregoing that the finger guide is designed to require that the finger of the person to be classified is correctly seated each time a classification is to be made, thus, providing the reproducibility desired for repetitious classifications. It may be seen that a similar result could be achieved by having the finger guide slide down an inclined surface. However, this technique would not provide the desired result if a tape system were to be used such as the one shown in FIG. 7.

Figure 7:
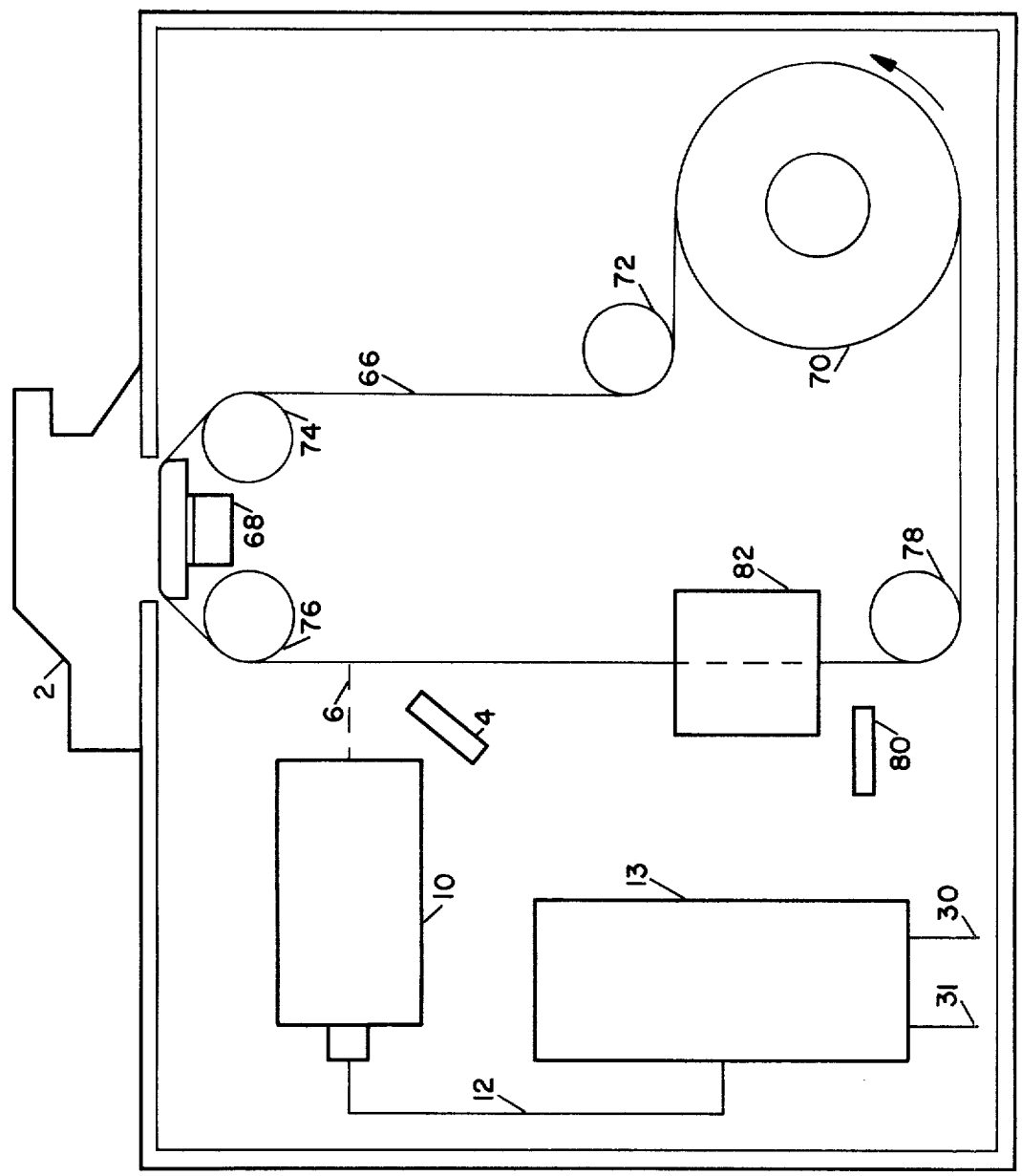
FIG. 7 is a simplified diagram of another embodiment of the invention in which the fingerprint image is first placed upon a tape before the classification process is initiated.

In FIG. 7 it may be seen that activator 2 includes the base member 46 and finger guide 42 including recess 48, but does not include optical tube 54, nor light sources 56. Further, activator 2 is mounted above tape guide 68 which provides a smooth flat surface immediately below aperture 40 so that a fingerprint will be impressed upon tape 66 when the finger is correctly aligned in finger guide 42. At this time the circuit is energized and delay 44 now provides an additional function in that the tape drive 58 is held inoperable until the finger pressure is removed. This is necessary to avoid smearing the fingerprint. Once the finger pressure has been removed tape drive 58 will move tape 66 in a counterclockwise direction until a tape frame indicator on the tape appears in front of tape frame register 80. At this time the fingerprint is positioned in the optical path 6 in front of image sensor 10 and the fingerprint is illuminated by light source 4. The pixels are transferred to evaluation circuit 13 for analysis as previously described. Roller guides 72, 74, 76 and 78 maintain the proper tension on tape 66. Tape conditioner 82 removes the fingerprint, if desired, and recoats the tape for reuse.

While the invention has been particularly shown and described with reference to preferred embodiments thereof, it will be understood by those skilled in the art that changes in form and detail may be made therein without departing from the spirit and scope of the invention. For example, in the tape system, it may be desireable to retain a copy of each fingerprint presented for classification. If so, conditioner 82 would not be required, but both a feed reel and a take up reel would be. Further, and end-of-tape indicator would be necessary and could be combined with a switch which would prevent operation if the tape tension indicated an end-of-tape condition. Also, the light transmission system could be modified to use lenses or fiber optics so that the relationship between the activator and the other portions of the system could take other forms; and could in fact be separated one from the other.

What is claimed is:

1. Apparatus for classifying personnel by means of fingerprints to determine whether or not they are authorized which comprises:

means for storing fingerprint characteristics of authorized personnel; activating means comprising:

indexing means having a recessed groove shaped to accept a finger of the person to be classified, and having an aperture at the bottom of the groove shaped to display the fingerprint image, said indexing means requiring both forward and downward pressures to properly seat the finger and to make the fingerprint portion visible through said aperture, said indexing means returning to the original position when the finger is withdrawn thereby removing the forward and downward pressures; and switch means for completing electrical circuits whereby said apparatus is energized when the finger has been properly aligned by the insertion in said recessed groove and by the application of said forward and downward pressures;

Opto-electronic means for reading the fingerprint characteristic of the person to be classified; and means for comparing the image fingerprint characteristic with the stored fingerprints to determine if the image fingerprint is one of those authorized.

2. Apparatus as set forth in claim 1, wherein said opto-electronic means further comprises:

means for displaying the image fingerprint; and means for electronically scanning the displayed optical image and for providing an electrical signal output representative of the image fingerprint.

3. Apparatus as set for in claim 2 wherein said means for displaying further comprises:

lighting means for illuminating the fingerprint during scanning by said electronic means; and delay means responsive to said switch means for providing a separate electrical connection to the electrical circuit closed for a predetermined time after the pressures applied to said indexing means have been removed, whereby the classification may be completed even though the finger has been removed.

4. Apparatus as set forth in claim 3 wherein said means for activating further comprises:

an oval shaped aperture in said indexing means, thus, causing a portion of the finger to protrude through said indexing means.

5. Apparatus as set forth in claim 4, wherein said opto-electronic means further comprises:

means for displaying the image fingerprint; and means for electronically scanning the displayed optical image and for providing an electrical signal output representative of the image fingerprint.

* * * * *